United States Patent [19]

[11] Patent Number: 6,121,343
[45] Date of Patent: Sep. 19, 2000

[54] PERFUME-CONTAINING CONTROLLED RELEASE RESIN COMPOSITION

[75] Inventors: Hideyuki Hongo; Yoji Hori; Yasuo Fujiwara; Seiichi Abe; Minoru Hanada, all of Kanagawa, Japan

[73] Assignee: Takasago International Corporation, Tokyo, Japan

[21] Appl. No.: 09/162,506

[22] Filed: Sep. 29, 1998

[30] Foreign Application Priority Data

Oct. 3, 1997 [JP] Japan .................................... 9-287661

[51] Int. Cl.[7] ............................................. A61K 31/765
[52] U.S. Cl. ..................................... 523/102; 424/78.37
[58] Field of Search ......................... 523/102; 428/78.37

[56] References Cited

U.S. PATENT DOCUMENTS

| 4,587,129 | 5/1986 | Kliment ............................ 426/534 |
| 4,842,761 | 6/1989 | Rutherford ......................... 252/90 |
| 5,631,344 | 5/1997 | Hongo et al. ...................... 528/283 |

FOREIGN PATENT DOCUMENTS

| 6-107838 | 9/1992 | Japan . |
| 8-53540 | 6/1994 | Japan . |
| 8-127645 | 10/1994 | Japan . |

*Primary Examiner*—Kriellion Sanders
*Attorney, Agent, or Firm*—Sughrue, Mion, Zinn, Macpeak & Seas, PLLC

[57] ABSTRACT

A perfume-containing controlled release biodegradable resin composition which can release aroma of the included perfume gradually without changing its perfume tone and can be used in such applications as deodorants, etc. The resin composition includes a biodegradable resin which is a random or block copolymer polyester represented by the following formula (1):

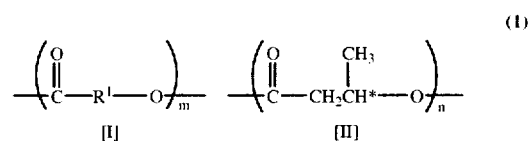

wherein $R^1$ is a hydrocarbon radical having 1 to 15 carbon atoms, which is a divalent organic group that may be have a double bond or an oxygen atom but does not have a group represented by the formula

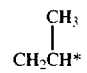

wherein the symbol "*" is an asymmetric carbon atom. Each of m and n is 0 or an integer of 100 to 9,000, provided that m+n is within the range of 200 to 10,000. The molar ratio of the structural units [I] and [II] is 1-99:99-1 when m and n are not 0 and the number average molecular weight is 5,000 to 1,000,000, and a perfume such as a cyclic ether, a natural plant perfume, etc., is held in the biodegradable resin.

6 Claims, No Drawings

PERFUME-CONTAINING CONTROLLED RELEASE BIODEGRADABLE RESIN COMPOSITION

FIELD OF THE INVENTION

This invention relates to a biodegradable resin composition which contains a perfume, more particularly to a perfume-containing controlled release biodegradable resin composition in which the perfume included in the biodegradable resin can be released gradually for a prolonged period of time without changing the perfume tone of the perfume itself.

BACKGROUND OF THE INVENTION

Aerosols, gel products, solutions, powders, synthetic resin products and the like are known in the prior art as the forms of aromatics, deodorants, antimicrobial agents and the like, and a number of attempts have been made particularly to adhere or include perfumes and the like aromatic substances to or in synthetic resins. In general, since there is no compatibility between aromatic substances and synthetic resins, an aromatic substance included in a resin exudes therefrom to the resin surface and rapidly lose its effects or the aromatic substance is sealed in the resin and does not diffuse to the surface, so that the effects expected as an aromatic cannot fully be exerted. For example, chain hydrocarbon based thermoplastic resins such as polyethylene and polypropylene are inferior in gas permeability and styrene based and polyvinyl acetate based resins have too much gas permeability, so that all of these resins are not suitable as base materials for aromatic substances.

With the aim of resolving these disadvantages of synthetic resin products, various methods have been proposed, such as a method in which an aromatic substance is supported on a hydrophilic polymer such as an hydrophilic acrylate or hydrophilic methacrylate (JP-B-49-4946: the term "JP-B" as used herein means an "examined Japanese patent publication"), a method in which a chlorine compound of polyethylene or a polyethylene copolymer is used (JP-B-50-29015), a method in which a low molecular weight polyolefin resin is mixed with a perfume and melted, and the resulting pellets are mixed with a high molecular weight polyolefin resin (JP-B-54-37974) and a method in which a perfume is entrapped in a copolymer of ethylene with vinyl acetate or various acrylic esters (JP-B-53-98352) or absorbed therein by impregnation (JP-B-56-121560). Also proposed is a resin composition for aromatic material use in which a perfume evaporation controlling agent such as benzyl benzoate is included in an ethylene-vinyl acetate copolymer (JP-B-63-6099).

Though there are products already realized as aromatics and deodorants by including aromatic substances in these synthetic resins to be used as base materials, almost all of these synthetic resins described above have no biodegradability and are not easily be decomposed when left in the natural environment after their use, so that they become a cause of environmental pollution. In consequence, it is desirable to recover them after use and carry out their incineration or recycling, but such operations impose a large economical burden.

As a method for resolving such a problem, products which do not violate the natural environment have positively been proposed by the use of a synthetic resin as the base material which has so-called biodegradability that renders possible easy decomposition of the resin making use of microorganisms distributed in the natural world.

Recently, several aromatics, deodorants, antimicrobial agents and the like have been proposed in which synthetic resins having biodegradability are used as the base material. For example, a biodegradable expansion molding product comprised of wheat flour, starch and water (JP-A-5-320401: the term "JP-A" as used herein means an "unexamined published Japanese patent application"), a volatile drug-containing material comprised of porous cellulose (JP-A-6-65412), a perfume-containing foam comprised of pulp (JP-A-6-107838) and the like have been proposed, but all of these synthetic resins used as the base material lack in transparency and cannot yet be said practically useful in terms of their compatibility with aromatic substances and hardness, strength and the like of the resins.

In addition, an antimicrobial composition in which an antimicrobial perfume, hinokitiol, is included in a low molecular weight lactic acid-glycolic acid copolymer has also been proposed (JP-A-5-97619), but having disadvantages in that the molding forms are restricted due to the low molecular weight of the material to be used as the base, the material itself is very apt to be hydrolyzed and controlled release of hinokitiol cannot be effected without accelerating decomposition of the base material because hinokitiol does not permeate through the base material easily.

SUMMARY OF THE INVENTION

With the aim of resolving the aforementioned problems, and taking note of the excellent characteristics such as biodegradability, hydrolyzing ability, workability and formability of the biodegradable resins disclosed in JP-A-8-53540 and JP-A-8-127645, the inventors of the present invention have conducted intensive studies on the combination of these biodegradable resins with perfumes and found as a result of their efforts that perfume-containing biodegradable resins obtained by including perfumes in these biodegradable resins can release the perfumes gradually for a prolonged period of time without changing the perfume tones of the perfumes themselves.

Accordingly, the present invention provides a perfume-containing controlled release biodegradable resin composition, which comprises a biodegradable resin comprised of a random or block copolymer polyester represented by the following formula (1):

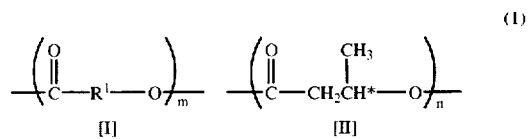

wherein $R^1$ represents a hydrocarbon group having 1 to 15 carbon atoms, which is a divalent organic group that may have a double bond or an oxygen atom but does not have a group represented by a formula

where the symbol "*" represents an asymmetric carbon atom, and each of m and n is 0 or an integer of from 100 to 9,000, with the proviso that m+n is within the range of from 200 to 10,000, wherein the molar ratio of the structural units [I] and [II] is from 1-99:99-1 when m and n are not 0 and a number-average molecular weight of the polyester is from 5,000 to 1,000,000, and a perfume held in said biodegradable resin.

Other objects and advantages of the present invention will be made apparent as the description progresses.

DETAILED DESCRIPTION OF THE INVENTION

The perfume to be used in the present invention is not particularly limited, with the proviso that it does not exert bad influences upon the characteristics of the resin and does not generate inconvenient changes in its compatibility with the resin and perfume tone and perfume quality of the perfume itself, and it can be used by optionally selecting from liquid perfumes, powder perfumes, vegetable essential oils and the like.

Examples of such perfumes include cyclic ethers, ketones, alcohols, lactones, esters, aldehydes and natural plant perfumes, as well as a geranium-like mixed perfume, an ilang-ilang-like mixed perfume, a cyclamen-like mixed perfume, a floral-like mixed perfume, a pine needle-like mixed perfume, a hiba oil-like mixed perfume, a citrus fruit-like mixed perfume and the like.

Illustrative examples of perfumes classified into these substances are as follows.

That is, hexamethylhexahydrocyclopentabenzopyrane and rose oxide can be exemplified as cyclic ethers, α-isomethyl ionone a ketone, dipropylene glycol, cis-3-hexenol, linalool and dihydrofarnesol as alcohols, decalactone and γ-undecalactone as lactones, geranyl acetate, isobornyl acetate and hexyl salicylate as esters, citronellal, α-hexylcinnamic aldehyde and p-t-butyl-α-methylhydrocinnamic aldehyde as aldehydes and hinokitiol, armoise, lemon, lime, orange terpene, rosemary and the like as natural plant perfumes, and a geranium-like mixed perfume, a cyclamen-like mixed perfume, a pine needle-like mixed perfume, a hiba oil-like mixed perfume, a citrus fruit-like mixed perfume and the like can also be exemplified. These perfumes may be used alone or as a mixture of two or more as occasion demands.

The resin composition of the present invention is obtained by including various perfumes in a biodegradable resin represented by the aforementioned formula (1), and the biodegradable resin to be used as the base material can be produced in accordance with the methods disclosed in JP-A-8-53540 and JP-A-8-127645.

Firstly, optically active (R)-β-butyrolactone (to be referred to as (R)-β-BL hereinafter) and (S)-β-butyrolactone (to be referred to as (S)-β-BL hereinafter) as the raw materials of poly(3-hydroxybutyric acid) which is one of the structural units of the polyester of the present invention can be obtained easily in accordance with the methods disclosed in JP-A-6-128245, JP-A-7-188201 and JP-A-7-206885, namely by carrying out asymmetric hydrogenation of diketene using a ruthenium-optically active phosphine complex as a catalyst. Also, racemic butyrolactone (to be referred to as β-BL hereinafter) is easily available as a commercial product.

Next, in describing the lactones which constitute the structural unit [II] as a material of said polyester, optically active (R)-β-valerolactone and (S)-β-valerolactone can be obtained for example from optically active methyl-3-hydroxyvaleric acid through 4 steps in accordance with the method of Y. Zhang et al. (*Macromoleules*, 23, 3206, 1990). Also, optically active (R)-7-methyl-1,4-dioxepan-5-one or (S)- 7-methyl-1,4-dioxepan-5-one can be obtained for example by the method disclosed in JP-A-4-316575, namely from optically active methyl-3-hydroxybutyric acid through 3 steps.

In addition, α,α-dimethyl-β-propiolactone can be obtained in accordance, for example, with the method disclosed by Yamashita et al. (Koqyo Kagaku Zasshi (*Journal of Industrial Chemistry*), vol. 67, p. 252, 1964), and α,β-dimethyl-β-propiolactone can be obtained in accordance, for example, with the method disclosed by Dervan et. al. (*J. Org. Chemistry*, 44, 2116, 1979).

Examples of other lactones include lactones in which the divalent organic group ($R^1$) of the lactone is comprised of an alkylene group having 1 to 15 carbon atoms, such as β-butyrolactone (β-BL), β-ethyl-β-propiolactone, α-methyl-β-propiolactone, γ-butyrolactone, α-methyl-γ-butyrolactone, β-methyl-γ-butyrolactone, γ-methyl-γ-butyrolactone, δ-valerolactone, β-methyl-δ-valerolactone, ε-caprolactone, 15-pentadecanolide, 16-hexadicanolide and the like, lactones in which the divalent organic group of the lactone is comprised of an alkenyl group which has 1 to 15 carbon atoms and contains a double bond, such as 5,6-dihydro-2H-pyran-2-one, 3,4-dihydro-6-methyl-2H-pyran-2-one, 5,6-dihydro-6-methyl-2H-pyran-2-one, 9-hexadecen-16-olide and the like, and lactones in which the divalent organic group of the lactone is comprised of an alkyl group which has 1 to 15 carbon atoms and contains an ester group or an ether group, such as glycolide, L-lactide, DL-lactide, 1,4-dioxepan-5-one, 7-methyl-1,4-dioxepan-5-one, 12-oxa-16-hexadecanolide, 11-oxa-16-hexadecanolide, 10-oxa-16-hexadecanolide and the like.

Among these compounds, 15-pentadecanolide can be obtained for example in accordance with the method disclosed in *Org. Synth.*, vol. 58, p. 98 (1987), and 16-hexadecanolide can be obtained for example in accordance with the method disclosed in *J. Chem. Soc.*, p. 4580 (1965).

Also, 5,6-dihydro-2H-pyran-2-one can be obtained for example in accordance with the method disclosed in *Org. Synth.*, vol. 56, p. 49 (1977)

As these aforementioned lactones, commercially available compounds or synthesized products can be used, but it is desirable to use purified compounds, for example those which are purified by repeating a step in which they are mixed with calcium hydride and distilled, twice, and then preserved in an inert gas until their use.

According to the polyester of the present invention, racemic bodies or optically active forms of the aforementioned lactones are used, and two or more of them may be jointly used as occasion demands.

The polyester to be used in the perfume-containing controlled release biodegradable resin composition of the present invention can be obtained illustratively by charging (R)-β-BL, (S)-β-BL or β-BL, or other lactones, in a reaction vessel in the presence or absence of an inert solvent and in an atmosphere of nitrogen, argon or the like inert gas, adding a catalyst thereto and then carrying out 30 minutes to 5 hours of the reaction at 60 to 180° C. under ordinary pressure.

Also, the copolymer polyester to be used in the perfume-containing controlled release biodegradable resin composition of the present invention can be obtained illustratively by selecting two or more compounds from (R)-β-BL, (S)-β-BL or β-BL, or other lactones, charging them in a reaction vessel in the presence or absence of an inert solvent and in an atmosphere of nitrogen, argon or the like inert gas, adding a catalyst thereto and then carrying out 1 minute to 24 hours of the reaction at 60 to 180° C. under ordinary pressure. As an alternative method, one compound is selected from (R)-β-BL, (S)-β-BL or β-BL, or other lactones, the thus selected compound is charged in a reaction vessel in the presence or absence of an inert solvent and in an atmosphere of nitrogen, argon or the like inert gas, a catalyst is added thereto and then 1 minute to 5 hours of the reaction is carried out at 60 to 180° C. under ordinary pressure to complete a first step polymerization. Thereafter, a small amount of an inert solvent is added to the resulting solution to reduce its viscosity and then lactones different from the lactones used in the first step are added thereto to carry out an additional 2 to 48 hours of a second step reaction, thereby obtaining an AB type block copolymer polyester.

Also, ABA type, ABC type and the like block copolymer polyesters are obtained by a method similar to the just described second step in which the reaction is carried out by adding (R)-β-BL, (S)-β-BL or β-BL, or other lactones, are added to the AB type block copolymer polyester.

In addition, the random or block copolymer of the present invention represented by the formula (1) can be produced by carrying out serial ring-opening copolymerization of an optically active β-BL with cyclic carbonates in the presence of a catalyst. Examples of such cyclic carbonates include trimethylene carbonate, 2,2-dimethyltrimethylene carbonate, 2-methyltrimethylene carbonate, 3-methyltrimethylene carbonate, 2,3-dimethyltrimethylene carbonate, 2,4-dimethyltrimethylene carbonate, 2,3,4-trimethyltrimethylene carbonate, 2,3,3,4-tetramethyltrimethylene carbonate and the like. These cyclic carbonates can be obtained by adding dropwise triethylamine to a toluene solution of the corresponding diol and chloroethyl formate in an ice bath.

In the perfume-containing controlled release biodegradable resin composition of the present invention, the aforementioned polyesters may be used alone or as a mixture of two or more, and, as occasion demands, additives such as boron nitride, talc and reinforcing fibers may be optionally selected and mixed. In general, there are effective resins among biodegradable resins such as a polyester composed of a dibasic acid and a diol, a polylactic acid, a polyglycolic acid and a copolymer of a polylactic acid with a polyglycolic acid, and their controlled release effect is increased by the joint use of the aforementioned polyester. With regard to the catalyst which is used in producing the perfume-containing controlled release biodegradable resin composition of the present invention, a tin catalyst, an aluminum catalyst, a zinc catalyst, a titanium catalyst and the like can beexemplified. Preferred among these catalysts is a tin catalyst, and its examples include dibutyltin oxide, dioctyltin oxide, dibutyltin dichloride, dioctyltin dichloride, tin dioctylate, dibutyltin dilauric acid, dibutyltin dimethoxide, dibutyltin diethoxide and the like.

A preferred example among these tin catalysts is a distannoxane catalyst represented by the following formula

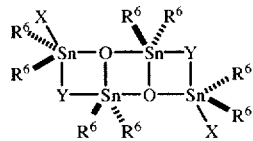

wherein $R^6$ is an alkyl group having 1 to 12 carbon atoms, an aralkyl group having 7 to 12 carbon atoms or a phenyl group, X is selected from the class consisting of a chlorine atom, a bromine atom and an isothiocyanate group, and Y is selected from the class consisting of a chlorine atom, a bromine atom, an isothiocyanate group, an hydroxyl group, a lower alkoxy group having 1 to 4 carbon atoms and a phenoxy group.

Illustrative examples of the distannoxane catalyst of the above formula include 1,3-dichlorotetramethyl distannoxane, 1,3-dichlorotetrabutyl distannoxane, 1,3-dichlorotetraphenyl distannoxane, 1,3-dichlorotetraoctyl distannoxane, 1,3-dichlorotetradodecyl distannoxane, 1,3-dibromotetrabutyl distannoxane, 1-hydroxy-3-chlorotetramethyl distannoxane, 1-hydroxy-3-chlorotetrabutyl distannoxane, 1-hydroxy-3-chlorotetraoctyl distannoxane, 1-hydroxy-3-chlorotetradodecyl distannoxane, 1-hydroxy-3-bromotetrabutyl distannoxane, 1-methoxy-3-chlorotetramethyl distannoxane, 1-methoxy-3-chlorotetrabutyl distannoxane, 1-methoxy-3-chlorotetraoctyl distannoxane, 1-ethoxy-3-chlorotetramethyl distannoxane, 1-ethoxy-3-chlorotetrabutyl distannoxane, 1-ethoxy-3-chlorotetraoctyl distannoxane, 1-phenoxy-3-chlorotetramethyl distannoxane, 1-phenoxy-3-chlorotetrabutyl distannoxane, 1-phenoxy-3-chlorotetraoctyl distannoxane, 1-methoxy-3-bromotetramethyl distannoxane, 1-methoxy-3-bromotetrabutyl distannoxane, 1-methoxy-3-bromotetraoctyl distannoxane, 1-ethoxy-3-bromotetramethyl distannoxane, 1-ethoxy-3-bromotetrabutyl distannoxane, 1-ethoxy-3-bromotetraoctyl distannoxane, 1-phenoxy-3-bromotetrabutyl distannoxane, 1-phenoxy-3-bromotetraoctyl distannoxane, 1-hydroxy-3-(isothiocyanate)tetramethyl distannoxane, 1-hydroxy-3-(isothiocyanate)tetrabutyl distannoxane, 1-hydroxy-3-(isothiocyanate)tetraoctyl distannoxane, 1-hydroxy-3-(isothiocyanate)tetradodecyl cistannoxane, 1-methoxy-3-(isothiocyanate)tetramethyl distannoxane, 1-methoxy-3-(isothiocyanate)tetrabutyl distannoxane, 1-methoxy-3-(isothiocyanate)tetraoctyl distannoxane, 1-methoxy-3-(isothiocyanate)tetradodecyl distannoxane, 1-ethoxy-3-(isothiocyanate)tetramethyl distannoxane, 1-ethoxy-3-(isothiocyanate)tetrabutyl distannoxane, 1-ethoxy-3-(isothiocyanate)tetraoctyl distannoxane, 1-ethoxy-3-(isothiocyanate)tetradodecyl distannoxane, 1-phenoxy-3-(isothiocyanate)tetramethyl distannoxane, 1-phenoxy-3-(isothiocyanate)tetrabutyl distannoxane, 1-phenoxy-3-(isothiocyanate)tetraoctyl distannoxane, 1,3-bis(isothiocyanate)tetramethyl distannoxane, 1,3-bis(isothiocyanate)tetrabutyl distannoxane, 1,3-bis(isothiocyanate)tetraoctyl distannoxane, 1,3-bis(isothiocyanate)tetradodecyl distannoxane and the like.

These distannoxane catalysts can be synthesized easily for example by carrying out reaction of dibutyltin oxide with dibutyltin diisothiocyanate in ethanol, as described in J. Organometallics, 3, 745 (1984) in the case of 1,3-dichlorotetraphenyl distannoxane or in J. Org. Chem., vol. 56, p. 5307 (1991) in the case of 1-hydroxy-3-(isothiocyanate)tetrabutyl distannoxane.

Examples of other compounds useful as the tin compound include 1,1-dibutylstanna-2,5-dioxacyclopentane, 1,1-dioctylstanna-2,5-dioxacyclopentane, 4,4-spirobis[1,1-dibutylstanna-2,6-dioxacyclohexane], 4,4-spirobis[1,1-dioctylstanna-2,6-dioxacyclohexane], methyl 2,3-O-,4,6-O-bis(dibutylstannylene)-β-D-glucopyranoside, methyl 2,3-O-,4,6-O-bis(dioctylstannylene)-β-D-galactopyranoside, methyl 2,3-O-,4,6-O-bis(dioctylstannylene)-α-D-glucopyranoside and the like.

In producing the polyesters, copolymer polyesters and block copolymer polyesters, at least one of these distannoxane catalysts is optionally selected and used, but, as occasion demands, two or more of them may be optionally selected and used in combination.

According to the present invention, each of the catalysts including distannoxane catalysts is used in an amount of generally from 1/500 to 1/40,000 mol, preferably from 1/1,000 to 1/20,000 mol, based on the material monomers.

In addition, the solvent to be used in the present invention is not particularly limited, with the proviso that it is a solvent used in general ring-opening polymerization, and its illustrative examples include straight or cyclic ethers such as diisopropyl ether, tetrahydrofuran and 1,4-dioxane, organic halides such as methylene bromide and dichloroethane, aromatic compounds such as toluene, benzene and xylene and mixed solvents thereof. It is desirable to purify commercially available solvents for example by their distillation in the presence of metallic sodium and benzophenone in an atmosphere of an inert gas and to store the thus purified solvents in an atmosphere of an inert gas until their use.

Next, when melt extrusion is employed as the method for molding the biodegradable resin to be used in the present invention, it is desirable to carry out the molding at a melting temperature of generally from 30 to 220° C., preferably from 60 to 200° C., though it may vary depending on the viscosity and melting point of the biodegradable resin to be used as the base material. The melting temperature if less than 30° C. would cause a difficulty in performing melt extrusion due to poor fluidity of the resin, and the melting temperature if exceeding 220° C. would cause a difficulty in obtaining a base material keeping the desired characteristics of the biodegradable resin because of significant decomposition of the biodegradable resin itself.

Also, when solvent casting is carried out, dichloromethane, chloroform, dichloroethane or the like halogen solvent or ethyl acetate, methanol or the like can be used as the solvent with no particular limitation, provided that it does not cause changes in the biodegradable resin. Preferably, the moldings obtained by the solvent casting of biodegradable resin are thoroughly air-dried and then the solvent is completely removed under vacuum.

According to the present invention, in order to improve workability and the like physical properties by quickening the recrystallization speed, nucleating agents and additives such as talc, boron nitride, titanium oxide, micro-mica and chalk may be added in an amount of from 0.01 to 10% by weight as occasion demands.

Next, with regard to the method for including a perfume in the thus molded biodegradable resin, kneading, dipping, coating and the like methods may be optionally selected, by taking into consideration the objects of use, the forms, conditions and the like of the final product.

When a perfume is included in the biodegradable resin by kneading, the aforementioned melt extrusion method can be applied. For example, a perfume-containing controlled release biodegradable resin composition can be obtained by mixing a perfume with the biodegradable resin and then subjecting the mixture to extrusion molding at a melting temperature of from 30 to 220° C., preferably from 60 to 200° C.

In the case of dipping, it may be effected by dipping the biodegradable resin in a container charged with a perfume, but, as occasion demands, it is desirable to pull out said biodegradable resin before it dissolves. The dipping time of the biodegradable resin and the amount of the perfume to be used are not particularly limited, but, depending on the degree of affinity between the used perfume and biodegradable resin, namely when the impregnation speed of the biodegradable resin to be dipped with the perfume to be used is slow, it is necessary to carry out the dipping for a prolonged period of time until the desired strength of aroma is obtained. On the other hand, when the impregnation speed of the biodegradable resin to be dipped with the perfume to be used is quick, the dipping can be completed within a short period of time until the desired strength of aroma is obtained.

In the present invention, the perfume is preferably contained in the biodegradable resin composition in an amount of 0.05 to 50% by weight, particularly 0.1 to 30% by weight, based on the polyester biodegradable resin. If the content is less than 0.05% by weight, the strength of the perfume is difficult to develop and if it is more than 50% by weight, the preparation of the composition is complicated and thus it is uneconomical.

In the case of coating, the biodegradable resin is dissolved in a solvent, uniformly mixed with a perfume and then directly coated.

As the solvent to be used, a halogen solvent such as dichloromethane, chloroform or dichloroethane or ethyl acetate, methanol or the like can be used with no particular limitation concerning its kind and amount, but it is desirable to avoid a solvent which does not dissolve in or mix with the perfume to be used or a solvent which causes inconvenience for the perfume and biodegradable resin to be used.

Thus, since the perfume-containing controlled release biodegradable resin composition of the present invention can release aroma gradually for a prolonged period of time without changing the perfume tone of the included perfume itself, it finds versatile use in such applications as aromatics, deodorants, antimicrobial agents, repellents and the like in response to the characteristics of the perfumes to be used.

Also, since the perfume-containing controlled release biodegradable resin composition of the present invention has a broad melting temperature range of from 30 to 180° C., perfumes and the like to be included therein can be optionally selected in response to their components and properties. In addition, the composition of the present invention is markedly rich in utility, because its flavoring by impregnation can be carried out easily and simply, its transparency and hardness can be changed optionally and its coating by dissolving it in a solvent can be made, so that shapes, colors and the like of the final products can be selected at will in response to the objects of use and the place of use.

EXAMPLES

Examples, Comparative Examples and Test Examples are given below by way of illustration and not by way of limitation.

In this connection, analytical instruments and the like used in the following inventive, comparative and test examples are as follows.

Nuclear magnetic resonance (NMR): AM-400 type apparatus (400 MHz) (manufactured by Bruker, Inc.)

Molecular weight: D-2520 GPC Integrator (manufactured by Hitachi Ltd.)

Differential scanning calorimeter (DSC): DSC 50 (manufactured by Shimadzu Corporation)

Thermogravimetric analyzer (TGA): TGA 50 (manufactured by Shimadzu Corporation)

Melt kneading machine: 15 ø compact kneading machine (manufactured by Ooba Kikai)

Also, in the biodegradable polyesters used in Examples and Comparative Examples, weight-average molecular weight was shown by Mw, number-average molecular weight by Mn, glass transition point by Tg, melting point by Tm and decomposition temperature by Td.

Example 1

(1) Synthesis of Syndiotactic-poly(3-hydroxybutyric acid) (to be referred to as "syn-P(3HB)" hereinafter)

A 1.72 g (20 mmol) portion of β-BL and 2.8mg (0.0025mmol) of 1-ethoxy-3-chlorotetrabutyl distannoxane were charged in a 20 ml capacity reaction container and stirred at 100° C. for 8 hours in an atmosphere of argon. The thus formed product was dissolved in chloroform and added to a mixed solvent of diethyl ether:hexane=1:3 to effect re-precipitation, thereby obtaining a syn-P(3HB) polyester (Mn=180,000, Mw=320,000, Tg=4.4° C., Tm=76.3° C., Td=282.7° C.) having a syndiotacticity of 61%.

In this connection, the isotacticity and syndiotacticity were calculated from the integrated values of iso peak and syn peak of the NMR spectrum in the usual way.

(2) Preparation of Hinokitiol-containing syn-P(3HB) Polyester

A 1 g portion of the syn-P(3HB) polyester synthesized in the above step (1) was dissolved in 5 ml of methylene chloride to which was subsequently added 0.05 g of hinokitiol with a polyester weight ratio of 5%, and the resulting mixture was poured into a Petri dish of 6 mm in diameter and solidified by evaporating the solvent methylene chloride, thereby making the resulting residue into a disc-like shape of 0.2 to 0.22 mm in thickness. This was punched out using a hole punch of 6 mm in diameter to obtain discs of syn-P (3HB) polyester containing 5% hinokitiol.

Each of the thus prepared discs was found to have an average weight of 8.68 mg and a hinokitiol content of 434 μg.

Example 2

(1) Synthesis of Polycaprolactone (to be referred to as "PCL" hereinafter)

A 2.28 g (20 mmol) portion of ε-caprolactone, 2.0 ml of toluene and 2.8 mg (0.0025 mmol) of 1-ethoxy-3-chlorotetrabutyl distannoxane were charged in a 20 ml capacity reaction container and stirred at 100° C. for 30 minutes in an atmosphere of argon. The thus formed product was dissolved in chloroform and poured into a mixed solvent of diethyl ether:hexane=1:3 to effect re-precipitation, thereby obtaining a PCL polyester (Mn= 240,000, Mw=450,000, Tg=–70° C., Tm=62° C., Td=390° C.).

(2) Preparation of Hinokitiol-containing PCL Polyester

A 1 g portion of the PCL polyester synthesized in the above step (1) was dissolved in 5 ml of methylene chloride to which was subsequently added 0.05 g of hinokitiol with a polyester weight ratio of 5%, and the resulting mixture was poured into a Petri dish of 6 cm in diameter and solidified by evaporating the solvent methylene chloride, thereby making the resulting residue into a disc-like shape of 0.2 to 0.22 mm in thickness. This was punched out using a hole punch of 6 mm in diameter to obtain discs of PCL polyester containing 5% hinokitiol.

Each of the thus prepared discs was found to have an average weight of 10.1 mg and a hinokitiol content of 505 μg.

In the following Comparative Examples 1 to 3, hinokitiol-containing discs were prepared respectively using, (1) an ethylene-vinyl acetate copolymer (to be referred to as "EVA" hereinafter) which is used as a controlled release base material but has no biodegradability and is not soluble in water, (2) a polyvinyl alcohol (to be referred to as "PVA" hereinafter) which is used as a controlled release base material but has no biodegradability and is soluble in water, and (3) a polystyrene (to be referred to as "PS" hereinafter) which has no biodegradability but is a general purpose plastic, as the base materials.

In addition, a hinokitiol-containing disc was prepared using a filter paper as a control in Comparative Example 4.

Comparative Example 1

(Preparation of Hinokitiol-containing EVA)

A 1 g portion of EVA was dissolved in 5 ml of methylene chloride to which was subsequently added 0.05 g of hinokitiol with a EVA weight ratio of 5%, and the resulting mixture was poured into a Petri dish of 6 cm in diameter and solidified by evaporating the solvent methylene chloride, thereby making the resulting residue into a disc-like shape of 0.4 to 0.042 mm in thickness. This was punched out using a hole punch of 6 mm in diameter to obtain discs of EVA containing 5% hinokitiol.

Each of the thus prepared discs was found to have an average weight of 18.5 mg and a hinokitiol content of 925 μg.

Comparative Example 2

(Preparation of Hinokitiol-containing PVA)

A 2 g portion of PVA was dissolved in 10 ml of ethanol to which were subsequently added 0.15 g of hinokitiol with a PVA weight ratio of 5% and then 1.0 g of propylene glycol and 10 ml of water, and the resulting mixture was poured into three Petri dishes of 6 cm in diameter and thoroughly solidified, thereby making the resulting residue into a disc-like shape of 0.2 to 0.22 mm in thickness. This was punched out using a hole punch of 6 mm in diameter to obtain discs of polyvinyl alcohol containing 5% hinokitiol.

Each of the thus prepared discs was found to have an average weight of 9.18 mg and a hinokitiol content of 495 μg.

Comparative Example 3

(Preparation of Hinokitiol-containing PS)

A 1 g portion of PS was dissolved in 5 ml of methylene chloride to which was subsequently added 0.051 g of hinokitiol with a PS weight ratio of 5%, and the resulting mixture was poured into a Petri dish of 6 cm in diameter and solidified by evaporating the solvent methylene chloride, thereby making the resulting residue into a disc-like shape of 0.2 to 0.22 mm in thickness. This was punched out using a hole punch of 6 mm in diameter to obtain discs of polystyrene containing 5% hinokitiol.

Each of the thus prepared discs was found to have an average weight of 8.48 mg and a hinokitiol content of 424 μg.

Comparative Example 4

Hinokitiol was dissolved in ethanol to prepare a 50 mg/ml solution, and 5 μl×2 of the solution was added dropwise using a syringe to a filter paper (Toyo Roshi No. 2) that has been punched out using a hole punch of 6 mm in diameter and then dried to remove the solvent ethanol, thereby obtaining a control disc.

The thus prepared disc contained 500 μg of hinokitiol.

Test Example 1(Controlled release test)

Method: The controlled release test was carried out by an agar plate method in which *Staphylococcus epidermidis* JCM 2414 was used as the test strain. The agar plate was prepared by sterilizing Mueller Hinton Medium (DIFCO) which has been supplemented with 3% of sodium chloride, cooling the medium to about 50° C., mixing the thus cooled medium with an appropriate amount of cell suspension of the test strain, dispensing the resulting mixture in 10 ml portions into Petri dishes of 9 cm in diameter and then solidifying the agar at room temperature. The hinokitiol-containing discs respectively prepared in Example 1 (2), Example 2 (2) and Comparative Examples 1 to 4 were put on the agar plate to carry out 17 hours of culturing. The amount of dispersed hinokitiol was determined by comparing the inhibition zone formed by each of the test discs with the inhibition zone formed by the control disc (Comparative Example 4). A total of 5 discs were used for each test and their average value was calculated. The minimum amount of hinokitiol determinable by this method was 2 μg/disc.

By repeating this procedure, cumulative time until dispersion of hinokitiol from each disc became not determinable was calculated and used for the evaluation of the controlled release effect.

Results: The results are shown in Table 1.

The degree of biodegradation was calculated by the following formula.

Degree of biodegradation=(amount of carbon dioxide actually generated÷amount of carbon dioxide theoretically calculated)× 100

(Note) When it is assumed that the carbon content of syn-P(3HB) polyester molecule is 55.4% and the carbon content of cellulose molecule is 43.5%, and that all of the carbon atoms are converted into carbon dioxide, amounts of generated carbon dioxide becomes 2.03 g and 1.60 g, respectively, per 1 g.

TABLE 1

| | Time Passed (h) | | | | | | | | | | | | |
|---|---|---|---|---|---|---|---|---|---|---|---|---|---|
| | 0 | 17 | 34 | 51 | 68 | 85 | 102 | 119 | 136 | 153 | 170 | 187 | 204 |
| Examples | | | | | | | | | | | | | |
| syn-P(3HB) | 434 | 78 | 33 | 23 | 20 | 21 | 13 | 9.3 | 9.5 | 6.5 | 6.1 | 3.9 | 4.4 |
| PCL | 505 | 83 | 46 | 37 | 29 | 26 | 15 | 9.1 | 5.6 | 3.7 | 2.7 | <2 | <2 |
| Comparative Examples | | | | | | | | | | | | | |
| EVA | 925 | 118 | 68 | 48 | 42 | 48 | 36 | 24 | 31 | 32 | 23 | 18 | 19 |
| PVA | 459 | 275 | — | — | — | — | — | — | — | — | — | — | — |
| PS | 424 | <2 | — | — | — | — | — | — | — | — | — | — | — |
| PPD | 500 | 500 | 3.8 | 1.9 | 1.5 | 1.9 | <2 | — | — | — | — | — | — |

| | Time Passed (h) | | | | | | | | | | | | |
|---|---|---|---|---|---|---|---|---|---|---|---|---|---|
| | 221 | 238 | 255 | 272 | 289 | 306 | 323 | 340 | 357 | 374 | 391 | 408 | 425 |
| Examples | | | | | | | | | | | | | |
| syn-P(3HB) | 4.0 | 2.6 | 2.9 | 2.3 | 2.2 | 1.8 | 1.5 | <2 | — | — | — | — | — |
| PCL | <2 | — | — | — | — | — | — | — | — | — | — | — | — |
| Comparative Examples | | | | | | | | | | | | | |
| EVA | 18 | 15 | 10.5 | 7.5 | 7.0 | 6.5 | 3.7 | 3.2 | 2.3 | <2 | <2 | — | — |

(Unit: μg/disc)
(Note) The symbol "—" means that the inhibition zone was not observed.

As is evident from the results shown in Table 1, the controlled release effect was observed over a total of 340 hours or more when the syn-P(3HB) polyester of the present invention was used, similar to the case of EVA which does not show biodegradability. Also, the controlled release effect was observed over a total of about 190 hours even when the PCL polyester of the present invention was used. This was followed by filter paper, PVA and PS in that order, but, being soluble in water, PVA swelled after 17 hours and cannot be measured thereafter. Also, controlled release effect was observed in PS until about 17 hours but not thereafter.

Test Example 2 (Biodegradability test)

Method: This was carried out in accordance with the test method of ISO CD14855. That is, using about 100 g of each of the syn-P(3HB) polyester used in the present invention and completely decomposable cellulose powder as a control, 60 days of the biodegradability test was carried out at 58° C. and the amount of generated carbon dioxide was measured.

Results: The results are shown in Table 2.

TABLE 2

| Test sample | Carbon content of polymer (%) | Released amount of gas per 1 g polymer (mg CO$_2$/g) | Average decomposition ratio (%) |
|---|---|---|---|
| syn-P(3HB) polyester | 55.4 | 1,255 | 61.7 |
| Control (cellulose) | 43.5 | 1,107 | 69.5 |

As is evident from the results shown in Table 2, the syn-P(3HB) polyester of the present invention showed 61.7% of biodegradation after 60 days, which was close to the value, 69.5%, of the biodegradation degree of cellulose. On the basis of these results, it can be said that the syn-P(3HB) polyester is a markedly excellent material which is possessed of almost the same degree of biodegradability of cellulose.

Test Example 3

(1) Preparation of Base Material for Test Piece Use

A 140 g portion of the syn-P(3HB) polyester synthesized in Example 1 (1) was put into a one liter capacity eggplant type flask and dissolved in 300 ml of methylene chloride at 40° C. using a rotary evaporator. Thereafter, the thus prepared solution was poured into a stainless steel vat and air-dried for 2 weeks, and the thus dried material was cut into a size of 21×21×1.8 mm and further dried under vacuum for 1 week in a desiccator to remove the solvent completely, thereby obtaining a base material for test piece use.

(2) Impregnation Test

Method: Three samples of the base material for test piece use were weighed (1.2 g in average weight), soaked in 18 g of each perfume in a 50 ml capacity screw-capped bottle and then took out after 2, 6 and 24 hours, and excess perfume remained on the surface was wiped up with tissue paper. Using the thus treated samples as test pieces, their weights were measured to calculate the rate of impregnation. In this case, the test was suspended when the test piece was dissolved by the perfume (degree of dissolution: cd, considerably dissolved; sd, slightly dissolved).

EVA and polyvinyl chloride (to be referred to as "PVC" hereinafter) were used as controls.

Results: The results are shown in Table 3.

TABLE 3

| Perfume | Item Rate of impregnation (%) Time | | |
|---|---|---|---|
| | 2 hr | 6 hr | 24 hr |
| <syn-P(3HB)> | | | |
| 1. ABBALIDE BB | 0.5 | 1.1 | 1.7 |
| 2. DECALACTONE | 1.6 | 3.0 | 5.1 |
| 3. γ-UNDECALACTONE | 3.2 | 6.1 | 11.1 |
| 4. ARMOISE OIL | 5.9 | 11.7 | 22.7 |
| 5. CITRONELLAL 85% DSP | 4.6 | 8.6 | 15.7 |
| 6. DL-ROSE OXILIDE | 2.3 | 4.3 | 7.9 |
| 7. DIPROPYLENE GLYCOL | 0.2 | 0.4 | 0.5 |
| 8. GAMMA METHYL IONONE T | 0.3 | 0.6 | 1.0 |
| 9. GERANIUM COMPOUND | 2.0 | 3.5 | 6.1 |
| 10. GERANYL ACETATE | 3.3 | 5.8 | 10.4 |
| 11. HEXYL CINNAMIC ALD. SP | 0.8 | 1.5 | 2.7 |
| 12. ISOBORNYL ACETATE | 1.1 | 2.0 | 3.6 |
| 13. LEAF ALCOHOL | 3.2 | 5.4 | 9.1 |
| 14. LEMON TERPENE | 0.6 | 1.0 | 1.6 |
| 15. LILIAL | 2.7 | 5.1 | 9.1 |
| 16. LIME OIL DIST MEXICO | 0.7 | 1.2 | 2.0 |
| 17. LINALOOL | 6.0 | 10.9 | 20.0 |
| 18. N-HEXYL SALICYLATE | 1.7 | 2.3 | 3.9 |
| 19. ORANGE TERPENE IMPORT | 0.3 | 0.5 | 0.8 |
| 20. ROSEMARY OIL SURESTE | 1.1 | 1.8 | 3.0 |
| 21. CITRUS COMPOUND | 1.5 | 2.6 | 4.4 |

TABLE 3-continued

| Perfume | Item Rate of impregnation (%) Time | | |
|---|---|---|---|
| | 2 hr | 6 hr | 24 hr |
| 22. CYCLAMEN COMPOUND | 1.6 | 2.5 | 4.3 |
| 23. DIHYDROFARNESOL | 0.09 | 0.10 | 0.11 |
| 24. PINE COMPOUND | 8.1 | 13.4 | 24.5 |
| 25. HIBA WOOD COMPOUND | 0.6 | 0.9 | 1.6 |
| <EVA> | | | |
| 14. LEMON TERPENE | 140 | sd 273 | cd 444 |
| 17. LINALOOL | 20.9 | 40.1 | 79.8 |
| 22. CYCLAMEN COMPOUND | 9.7 | 18.1 | 34.3 |
| 24. PINE COMPOUND | 42.1 | 86.1 | 162 |
| 25. HIBA WOOD COMPOUND | 55.8 | 122 | 284 |
| <PVC> | | | |
| 14. LEMON TERPENE | 0.08 | 0.10 | 0.13 |
| 17. LINALOOL | 0.00 | 0.00 | 0.00 |
| 22. CYCLAMEN COMPOUND | 0.00 | 0.00 | 0.00 |
| 24. PINE COMPOUND | 0.00 | 0.00 | 0.00 |
| 25. HIBA WOOD COMPOUND | 0.6 | 0.9 | 1.6 |

(3) Vaporization Test

Method: The test pieces after 24 hours of the just described impregnation test (2) were arranged on a tray by putting the central part of each test piece through a large drawing pin, and their weights were measured after 2, 6, 24 hours and 2, 5 and 15 days of standing at room temperature and under ordinary pressure to calculate the rate of vaporization.

Since certain test pieces having reduced weight due to their dissolution by perfumes and small impregnation rate of perfumes cause inaccurate values, their data until 24 hours are shown in ( ) and [ ].

When effects of humidity on these test pieces were tested together with controls to make corrections, a weight change of from +0.12 to −0.09% was found.

The rate of vaporization was calculated by the following formula.

Rate of vaporization=[(weight of test piece after 24 hours of impregnation with perfume)−(weight of test piece at predetermined time)]÷(weight of perfume with which base material for test piece use is impregnated)×100

Results: The results are shown in Table 4.

TABLE 4

| Perfume | Item Time | Rate of vaporization (%) | | | | | |
|---|---|---|---|---|---|---|---|
| | | 2 hrs | 6 hrs | 24 hrs | 2 days | 5 days | 15 days |
| <syn-P(3HB)> | | | | | | | |
| 1. ABBALIDE BB | | 1.7 | 2 | 2.3 | 5.1 | 12.6 | 29.7 |
| 2. DECALACTONE | | 21.2 | 32.4 | 47.2 | 55.4 | 66.9 | 81.5 |
| 3. γ-UNDECALACTONE | | 0.3 | 0.7 | 2.2 | 4.7 | 8.8 | 19.4 |
| 4. ARMOISE OIL | | 26.0 | 35.9 | 48.3 | 54.6 | 61.6 | 70.9 |
| 5. CITRONELLAL 85% DSP | | 18.0 | 32.9 | 52.7 | 60.7 | 69.8 | 80.6 |
| 6. DL-ROSE OXILIDE | | 22.2 | 31.3 | 43.8 | 51.3 | 60.3 | 82.5 |
| 7. DIPROPYLENE GLYCOL | | 7.7 | 13.5 | 40.4 | 57.7 | 67.3 | 88.5 |
| 8. GAMMA METHYL IONONE T | | 13.7 | 22.4 | 36.3 | 47.9 | 68.9 | 91.2 |
| 9. GERANIUM COMPOUND | | 8.7 | 17.7 | 35.0 | 46.1 | 57.8 | 72.5 |
| 10. GERANYL ACETATE | | 3.7 | 7.0 | 17.2 | 30.3 | 51.3 | 72.3 |
| 11. HEXYL CINNAMIC ALD. SP | | 1.0 | 1.5 | 1.8 | 5.4 | 12.2 | 28.8 |
| 12. ISOBORNYL ACETATE | | 22.9 | 33.2 | 45.6 | 52.7 | 63.6 | 77.1 |

TABLE 4-continued

| Perfume | Time | Rate of vaporization (%) | | | | | |
|---|---|---|---|---|---|---|---|
| | | 2 hrs | 6 hrs | 24 hrs | 2 days | 5 days | 15 days |
| 13. LEAF ALCOHOL | | 21.0 | 31.7 | 45.8 | 53.7 | 63.5 | 76.2 |
| 14. LEMON TERPENE | | 14.9 | 23.2 | 36.3 | 45.8 | 63.1 | 78.6 |
| 15. LILIAL | | 0.8 | 1.4 | 2.3 | 5.2 | 9.1 | 12.2 |
| 16. LIME OIL DIST MEXICO | | 18.5 | 28.5 | 41.9 | 51.2 | 67.3 | 87.3 |
| 17. LINALOOL | | 15.2 | 29.9 | 46.7 | 54.0 | 61.3 | 71.7 |
| 18. N-HEXYL SALICYLATE | | 2.3 | 3.7 | 5.8 | 9.8 | 17.0 | 36.3 |
| 19. ORANGE TERPENE IMPORT | | 13.6 | 23.3 | 36.9 | 46.6 | 75.7 | 96.2 |
| 20. ROSEMARY OIL SURESTE | | 18.6 | 28.6 | 42.1 | 49.3 | 61.1 | 75.0 |
| 21. CITRUS COMPOUND | | 17.5 | 27.2 | 41.3 | 50.2 | 62.8 | 78.3 |
| 22. CYCLAMEN COMPOUND | | 3.1 | 6.2 | 13.8 | 21.2 | 31.8 | 45.0 |
| 23. DIHYDROFARNESOL | | [4] | [8] | [18] | — | — | — |
| 24. PINE COMPOUND | | 11.5 | 21.3 | 39.5 | 49.0 | 58.1 | 68.5 |
| 25. HIBA WOOD COMPOUND | | 16.0 | 25.7 | 37.1 | 45.1 | 60.0 | 77.7 |

(4) Aroma Test

Method: The test pieces after 24 hours of the aforementioned impregnation test (2) were taken out 1, 5 and 15 days thereafter, and changes in their color tone and perfume tone were evaluated by sensory test carried out by three perfumers.

The evaluation was made by the following five step criteria for each item.

Strength of Aroma

5: very strong 4: strong 3: normal 2: weak 1: very weak

Changes in Perfume Tone

0: no changes
1: a difference is observed very slightly
2: a difference is observed to some extent
3: a difference is observed significantly
4: a difference is observed extremely Color Tone 0: no changes
1: slight changes
2: obvious changes
3: significant changes:
4: extreme changes Results: The results are shown in Table 5.

TABLE 5

| Item | | Strength of aroma | | | Changes in perfume tone | | | Discoloration |
|---|---|---|---|---|---|---|---|---|
| Perfume | Time (day) | 1 | 5 | 15 | 1 | 5 | 15 | 15 |
| <syn-P(3HB)> | | | | | | | | |
| 1. ABBALIDE BB | | 4 | 4 | 4 | 0 | 0 | 0 | 0 |
| 2. DECALACTONE | | 4 | 4–3 | 3 | 0 | 0 | 0 | 0 |
| 3. γ-UNDECALACTONE | | 4 | 4 | 4 | 0 | 0 | 0 | 0 |
| 4. ARMOISE OIL | | 4 | 4 | 2 | 0 | 0 | 3 | 0 |
| 5. CITRONELLAL 85% DSP | | 5 | 5 | 5 | 0 | 0 | 0 | 0 |
| 6. DL-ROSE OXILIDE | | 3 | 3 | 2 | 0 | 0 | 0 | 0 |
| 7. DIPROPYLENE GLYCOL | | 1 | 1 | 1 | 0 | 0 | 0 | 0 |
| 8. GAMMA METHYL IONONE T | | 4 | 4 | 4 | 0 | 0 | 0 | 0 |
| 9. GERANIUM COMPOUND | | 4–3 | 3 | 3 | 0 | 0 | 0 | 0 |
| 10. GERANYL ACETATE | | 2 | 2–1 | 2–1 | 0 | 0 | 0 | 0 |
| 11. HEXYL CINNAMIC ALD. SP | | 3 | 2 | 2–1 | 0 | 1 | 1 | 0 |
| 12. ISOBORNYL ACETATE | | 2–1 | 1 | 1 | 3 | 4 | 4 | 0 |
| 13. LEAF ALCOHOL | | 4 | 4 | 4 | 0 | 0 | 0 | 0 |
| 14. LEMON TERPENE | | 2 | 2 | 2 | 0 | 1 | 1 | 0 |
| 15. LILIAL | | 4 | 4 | 4–3 | 0 | 0 | 0 | 0 |
| 16. LIME OIL DIST MEXICO | | 3–2 | 2 | 2 | 0 | 1 | 2 | 0 |
| 17. LINALOOL | | 2 | 2–1 | 2–1 | 0 | 0 | 0 | 0 |
| 18. N-HEXYL SALICYLATE | | 3 | 3–2 | 2 | 0 | 1 | 1 | 0 |
| 19. ORANGE TERPENE IMPORT | | 2–1 | 1 | 1 | 0–1 | 2 | 3 | 0 |
| 20. ROSEMARY OIL SURESTE | | 4 | 4 | 3 | 0 | 0 | 0 | 0 |
| 21. CITRUS COMPOUND | | 2 | 2–1 | 2–1 | 0 | 2 | 3 | 0 |
| 22. CYCLAMEN COMPOUND | | 3 | 2 | 2 | 0 | 0 | 1 | 0 |
| 23. DIHYDROFARNESOL | | 2 | 2 | 2 | 0 | 0 | 0 | 0 |
| 24. PINE COMPOUND | | 4 | 4 | 4 | 0 | 0 | 0 | 0 |
| 25. HIBA WOOD COMPOUND | | 4–3 | 4–3 | 3 | 0 | 0 | 0 | 0 |

Results of the impregnation test, vaporization test and aroma test are shown in Tables 3, 4 and 5, respectively.

In the impregnation test, it was confirmed that the resin composition of the present invention is possessed of superior rate of impregnation to that of PVC and can be impregnated with a broad range of perfumes. Also, in the vaporization test, the inventive resin composition of the present invention was able to release a broad range of perfumes gradually at a certain rate for a prolonged period of time, thus confirming its controlled release effect. In addition, since the controlled release was observed in broader range of perfumes than the case of the prior art polymers and the strength of aroma was maintained in the aroma test, the perfume-containing controlled release biodegradable resin composition of the present invention has the effect to maintain aroma without changing perfume tone of the perfumes themselves, so that it can be said that the resin composition of the present invention is excellent in terms of aroma-keeping ability and controlled release effect.

Also, the syn-P(3HB) polyester used in the present invention as the base material was completely free from the odor of the base material itself and did not cause changes in the perfume tone when various perfumes were used. On the contrary, the EVA which showed similar effect in terms of the controlled release effect generated considerably strong base material odors (acid odor, ester odor and the like) by it self and exerted bad influences upon the perfume tone in certain perfumes used, so that it was not usable for weakly aromatic perfumes.

In addition, it was found that PVC has a perfume selectivity, because the resin was not impregnated with certain types of perfumes.

With regard to the discoloration, changes were not observed in almost all of the perfumes used.

While the invention has been described in detail and with reference to specific embodiments thereof, it will be apparent to one skilled in the art that various changes and modifications can be made therein without departing from the spirit and scope thereof.

What is claimed is:

1. A perfume-containing controlled release biodegradable resin composition, which comprises a biodegradable resin comprised of a random or block copolymer polyester represented by the following formula (1):

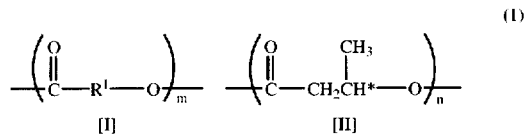

(1)

wherein $R^1$ represents a hydrocarbon group having 1 to 15 carbon atoms, which is a divalent organic group that may have a double bond or an oxygen atom but does not have a group represented by a formula

where the symbol "*" represents an asymmetric carbon atom, and each of m and n is 0 or an integer of from 100 to 9,000, with the proviso that m+n is within the range of from 200 to 10,000, wherein molar ratio of the structural units [I] and [II] is from 1-99:99-1 when m and n are not 0 and a number-average molecular weight of the polyester is from 5,000 to 1,000,000, and a perfume held in said biodegradable resin.

2. The perfume-containing controlled release biodegradable resin composition according to claim 1, wherein $R^1$ of the formula (1) is

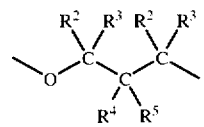

wherein $R^2$, $R^3$, $R^4$ and $R^5$ may be the same or different from one another and each represents a hydrogen atom or a methyl group.

3. The perfume-containing controlled release biodegradable resin composition according to claim 1, wherein the perfume is a liquid perfume, a powder perfume or a vegetable essential oil.

4. The perfume-containing controlled release biodegradable resin composition according to claim 2, wherein the perfume is a liquid perfume, a powder perfume or a vegetable essential oil.

5. The perfume-containing controlled release biodegradable resin composition according to claim 1, wherein the perfume has an antimicrobial action or a repellent action.

6. The perfume-containing controlled release biodegradable resin composition according to claim 2, wherein the perfume has an antimicrobial action or a repellent action.

* * * * *